United States Patent [19]

Martini et al.

[11] 4,136,121

[45] Jan. 23, 1979

[54] PROCESS FOR THE PREPARATION OF FLUORINE-CONTAINING KETONES

[75] Inventors: Thomas Martini, Bad Soden am Taunus; Friedhelm Kluge, Frankfurt am Main, both of Fed. Rep. of Germany

[73] Assignee: Hoechst Aktiengesellschaft, Frankfurt am Main, Fed. Rep. of Germany

[21] Appl. No.: 844,049

[22] Filed: Oct. 20, 1977

[30] Foreign Application Priority Data

Oct. 23, 1976 [DE] Fed. Rep. of Germany ....... 2648123
Feb. 4, 1977 [DE] Fed. Rep. of Germany ....... 2704607

[51] Int. Cl.$^2$ ............................................. C07C 49/04
[52] U.S. Cl. ............................ 260/593 H; 260/340.6; 260/594
[58] Field of Search ............................ 260/594, 593 H

[56] References Cited

U.S. PATENT DOCUMENTS

| | | | |
|---|---|---|---|
| 3,012,069 | 12/1961 | Drysdale | 260/593 H |
| 3,240,811 | 3/1966 | Drysdale | 260/593 |
| 3,513,203 | 5/1970 | Sianesi et al. | 260/594 |

OTHER PUBLICATIONS

Migndichian, Organic Synthesis, p. 123, Reinhold Publishing Corp. 1957.

*Primary Examiner*—Ethel G. Love
*Attorney, Agent, or Firm*—Curtis, Morris & Safford

[57] ABSTRACT

Perfluorocarboxylic acid salts of a monovalent metal are reacted with perfluorocarboxylic acid fluorides in aprotic polar solvents. Perfluoroketones are obtained.

The salt of the perfluorocarboxylic acid can be replaced by alkali metal salts of formic acid, oxalic acid or of oxygen-containing mineral acids, the central atom of which is an element of the groups IIIA to VIIA of the periodic table and which mineral acid is weaker than trifluoroacetic acid. The same result is obtained if the anhydride of the perfluorocarboxylic acid is contacted with an alkali metal fluoride. The synthesized perfluoroketones are liquids of high chemical and thermal stability.

4 Claims, No Drawings

PROCESS FOR THE PREPARATION OF FLUORINE-CONTAINING KETONES

The present invention relates to a process for the preparation of perfluoroketones from perfluorocarboxylic acid fluorides.

It is known from U.S. Pat. No. 3,185,734 to convert highly fluorinated acid fluorides into fluorinated ketones with hexafluoropropene or perfluoroisobutylene at a temperature of from 50 to 250° C., in an autoclave, in the presence of fluoride ions. This process is advantageously carried out in polar solvents, for example acetonitrile. It seems however, that this reaction cannot be applied to other perfluorinated olefins of low molecular weight. Moreover, frequently perfluoronated olefins are not accessible. This process, consequently, has only a narrow application field.

There was therefore a need for a process that should be substantially more variable with regard to the feed products than the process of U.S. Pat. No. 3,185,734: a process that should be performed without using perfluoroolefins and that should yield perfluorinated organic ketones, especially those having a high boiling point.

A process has now been found for the preparation of aliphatic perfluoroketones, which comprises reacting a perfluorocarboxylic acid salt of the formula $$R_1\text{-}CO_2M \qquad \qquad II$$

wherein
$R_1$ represents a perfluoroalkyl radical having of from 2 to 50 carbon atoms, which may contain one or more ether oxygen linkages and
M is a metal selected from the group consisting of Li, Na, K, Rb; Cs and Ag,
with perfluorocarboxylic acid fluorides of the formula $$R_2\text{ - COF} \qquad \qquad III$$

wherein
$R^2$ is a perfluoroalkyl radical having of from 1 to 50 carbon atoms which may contain in addition one or more ether oxygen linkages,
in an aprotic solvent, at a temperature of from 20 to 200° C.

The reaction temperature is in the range of from 50 to 180° C., in particular of from 100 to 150° C. The pressure applied is not critical. However, the solvent should be present in a liquid state at the chosen reaction temperature.

The quantity of solvent is not critical. It generally ranges between 10 and 200% of the volume of the acid fluoride used.

The aliphatic perfluorinated ketones obtained correspond to the formula $$R'_1 - CO - R_2 \qquad \qquad I$$

wherein $R_1'$ is a perfluoroalkyl radical having of from 2 to 50 carbon atoms which contain in addition one or more ether oxygen linkages, and $R_2$ is defined as indicated above.

Frequently, $R_1'$ is identical with $R_1$. This is the case for example when using salts wherein $R_1$ represents the groups $C_2F_5$—, $(CF_3)_2CF$— and $C_3F_7OCF(CF_3)$—. In other cases $R_1'$ is isomeric with $R_1$. This is the case for example when using salts wherein $R_1$ represents the groups $CF_3(CF_2)_2$— and $CF_3(CF_2)_3$—. Generally a secondary radical $R_1'$ is formed from a primary radical $R_1$ thereby.

The reaction according to the invention takes place according to the following equation:

$$R_1\text{—C(O)—OM} + F\text{—C(O)—}R_2 \rightarrow R_1'\text{—C(O)—}R_2 + CO_2 + MF$$

II III I

The radicals $R_1$ and $R_2$ may be linear, branched and/or cyclic. If these radicals contain oxygen atoms in ether groups, preference is given to those containing of from 3 to 25, in particular of from 5 to 20 carbon atoms. This is especially applicable to $R_1$.

Among perfluoroalkyl radicals free from oxygen preference is given to those which contain at least 2, preferably of from 3 to 8, carbon atoms. This is especially applicable to $R_1$.

The number of oxygen atoms in ether linkages which may be present in each of the radicals $R_1$ and $R_2$ may, for example, be half the number of the carbon atoms of the radical (the radical of the polymer of perfluoroethylene epoxide) or about one third (the radical of the polymer of perfluoropropene epoxide).

Suitable compounds of the formula III are those containing the structural element F-C-C-CO-F, especially in the form of —$CF_2CF_2COF$ or —$CF(CF_3)COF$, the free valencies being saturated by fluorine, perfluoroalkyl or perfluoroalkoxy radicals. The latter radicals may additionally contain one or several oxygen atoms as ether groups.

As examples of $R_1$ and $R_2$ there may be mentioned: perfluoropropyl, perfluorobutyl, perfluoropentyl, perfluoroheptyl, perfluorononyl, perfluoro-1-methyl-2-oxa-propyl, perfluoro-1-methyl-2-oxa-butyl, perfluoro-1-methyl-2-oxa-pentyl, perfluoro-1,3-dimethyl-2-oxa-butyl, perfluoro-1,4-dimethyl-2,5-dioxaoctyl, perfluoro-1-methyl-2-oxa-hexyl, -heptyl, -octyl, perfluoro-1,4,7-trimethyl-2,5,8-trioxaundecyl as well as the radicals of the formula

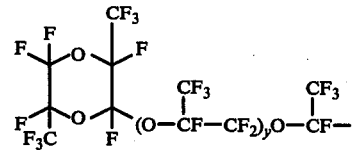

wherein Y is an integer of from 0 to 5.

A part of the compounds of the formulae II and III is known, the other part may be obtained according to known processes. For example, acid fluorides III having ether-like bound oxygen atoms may be prepared by reacting hexafluoropropene-epoxide with aliphatic, perfluorinated carboxylic acid fluorides (cf. U.S. Pat. Nos. 3,250,808; 3,321,532). The products thus obtained have the general formula

Especially appropriate for the process of the invention are acid fluorides of the formula IIIa, wherein the perfluorinated alkyl radical $R_f$ contains from 1 to 10, preferably 3 carbon atoms, and X represents an integer of from 1 to 6.

The alkali metal salts of the corresponding perfluorocarboxylic acids may be prepared from the acid fluorides III and IIIa in simple and known manner, by reaction with aqueous alkali metal hydroxide or aqueous alkali metal carbonate. Alkali metal fluorides formed in the process do not detrimentally affect the further reaction.

Suitable solvents for the process of the invention are aprotic polar solvents, for example amides, such as dimethylformamide or dimethylacetamide. Tetramethylurea and hexamethylphosphoric acid triamide may also be used. Preference is given to alkyl glycol ethers, for example dialkyl ether of glycol, of di-, tri- or tetraethylene glycol with alkyl groups having 1 or 2 carbon atoms.

Especially appropriate are diethylene-glycol-dimethyl ether (diglyme) and tetraethylene-glycol-dimethyl ether (tetraglyme).

The process of the invention is generally performed in the following manner: About equimolar quantities of both reaction components II and III are introduced into a reaction vessel together with the solvent and the mixture is stirred at the reaction temperature until completion of the reaction.

The end of the reaction can be seen by the fact that $CO_2$ is no longer evolved. When using an excess of the salt II, the end of the reaction can moreover be recognized by the fact that acid fluoride can no longer be detected by IR-spectroscopy (disappearance of the acid fluoride band at 5.3 μ as in Example 6 below). However, it is advantageous to use an excess of acid fluoride for obtaining a quantitative conversion.

The excess is suitably in the range of from 5 to 30%, in particular of from 10 to 20%. The excess of acid fluoride can be separated from the ketone by distillation and recovered upon completion of the reaction.

The process according to the invention may also be performed using acid fluorides of perfluorinated dicarboxylic acids. Acid fluorides of this type may be obtained inter alia according to German Offenlegungsschrift No. 2,451,493. Thus perfluorinated diketones are formed, since both acid fluoride groups react.

The mixture consisting of salts of the formula II and of acid fluorides of the formula III may alternatively be prepared by mixing perfluorinated acid anhydrides with alkali metal fluoride (NaF, KF, RbF, CsF). Thereby an equilibrium is set up between the acid anhydride on the one hand and salt plus acid fluoride on the other hand. The fact that this equilibrium is indeed shifted towards the components salt/acid fluoride, can be seen in the course of the reaction between potassium fluoride and perfluoroacetic acid anhydride. In this process there are formed instantaneously potassium trifluoroacetate and trifluoroacetyl fluoride according to the equation:

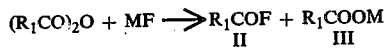

$$(R_1CO)_2O + MF \longrightarrow \underset{II}{R_1COF} + \underset{III}{R_1COOM}$$

In the next step perfluoroketone I is formed from II and III according to the invention.

Like the synthesis of ketone from II and III the reaction of alkali metal fluoride with anhydride also takes place at a temperature of from 20 to 200° C., especially of from 50 to 180° C., preferably of from 100 to 150° C. The quantity of solvent is not critical either in this case. It generally ranges between 0.1 and 10, especially of from 0.2 and 2, parts by volume per part by volume of acid anhydride. The end of the reaction can be observed by IR-spectroscopy or by the fact that the $CO_2$ evolution is terminated.

The molar ratio of alkali metal fluoride and acid anhydride is not critical. The reaction rate is increased by using higher amounts of alkali metal fluoride. As a general principle catalytic amounts of fluoride are sufficient, since, during the formation of the ketone, alkali metal fluoride is formed anew. Amounts of from 0.01 to 10, preferably of from 0.1 to 5 and in particular of from 0.2 to 2 mols of alkali metal fluoride per mol of acid fluoride are suitable.

A possible explanation of the reaction course is that from the alkali metal salt of the acids used and the acid fluoride there is first formed the anhydride, which decarboxylates in the presence of formed KF.

Another possible explanation is that the perfluorocarboxylic acid salt II is first decarboxylated to give the vinyl compound which is then added to the acid fluoride III.

The salts to be used according to the invention of the formula II may alternatively be prepared in situ from acid fluorides by the action of certain basic compounds. It has now been found that the ketone formation can likewise be caused by the action of alkali metal salts of formic or oxalic acid or of salts of mineral oxygen acids, the central atom of which is an element of groups IIIA to VIIA of the periodic table and which are weaker than trifluoroacetic acid, on perfluorocarboxylic acid fluorides of the formula $R_1COF$ in an aprotic-polar solvent at a temperature of from 20 to 200° C.

Said salts convert the perfluorocarboxylic acid fluoride used into the alkali metal salt of the corresponding perfluorocarboxylic acid. The latter decarboxylates under the reaction conditions, probably while forming the corresponding perfluoroalkyl cation or perfluorovinyl ether. This intermediately formed compound reacts with a further molecule of perfluorocarboxylic acid fluoride in the presence of formed alkali metal fluoride to give the desired perfluoroalkylketone.

Suitable for the process of the invention are the alkali metal salts of those mineral oxygen acids which are weaker than the acid from which the perfluorocarboxylic acid fluoride is derived. Since there are only small differences in the acid strength of the individual aliphatic perfluorocarboxylic acids, it will be sufficient to consider those mineral acids which are weaker than trifluoroacetic acid, i.e., the pK value of which is greater than 0.16 (the $P_K$-value is defined as the negative logarithm of the dissociation constant of the acid in dilute aqueous solution).

Especially appropriate are oxygen acids, the central atom of which belongs to the second line of the perodic table (elements 5 to 7 and 9) or to the third line (elements 13 to 17). It is especially suitable if the electronegativity of the central atom of the oxygen acid ranges between 2.0 and 2.5.

Suitable salts for the process of the invention are, for example, besides alkali metal salts of oxalic acid and of formic acid, the alkali metal salts of tetraboric acid ($P_K$ value 4.0), of metasilic acid ($P_K$-value 9.7), of phosphorous acid ($P_K$-value of 2.0), of sulfurous acid ($P_K$-value 1.8) or of iodic acid ($P_K$-value 0.77). Only the pK-value of the acid's first dissociation step is important. Formates, oxalates, tetraborates and metal silicates are used preferably. In particular, when reacting alkali carbonates with the acid fluorides mentioned at a temperature of from 20 to 200° C. in aprotic-polar solvents, the corresponding alkali metal salts are formed. These salts, however, continue to react in most cases rapidly with acid fluoride according to the invention yielding the ketones I. This variant of the process according to the invention is represented by the following scheme:

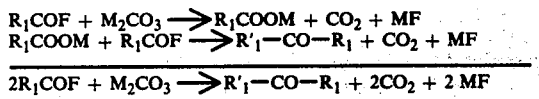

If the free acid, from which the alkali metal salt used is derived, has a lower $P_K$-value than the free acid from which perfluorocarboxylic acid fluoride is derived, the formation of the ketone can be observed, but very long reaction times and unsatisfactory yields are encountered. This is the case for sodium sulfate, for example, since sulfuric acid is a very strong acid ($P_K$-value < 10).

Most suitable are therefore salts of those acids which have a $P_K$-value in the range of from 0.16 to 10.0. The lower limit corresponds to the $P_K$-value of trifluoroacetic acid, which may be considered as being representative for perfluorinated carboxylic acids with regard to the acid number. Acids which have a $P_K$-value in the range of from 1 to 10 are preferably used. Salt mixtures may also be used naturally.

For forming a ketone molecule, one acid fluoride group generally requires one alkali metal ion.

The conversion with the salts of a monobasic mineral acid (for example iodic acid) may be represented by the following equation:

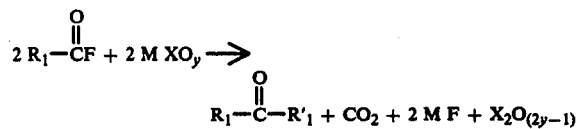

When using salts of bivalent mineral oxygen acids, the reaction equation may be formulated as in the case of the alkali metal carbonates.

The perfluorinated ketones I are substantially stable towards $SF_4$ and $UF_6$, especially if they have a higher molecular weight. They are not only inert towards acids and oxidants but also thermally stable.

According to German Offenlegungsschrift No. 25 31 511 perfluorinated ketones containing ether groups may be decarbonylated in liquid phase, i.e., be converted into perfluorinated ethers, by photolysis with light having a wave length of from 180 to 600 nm.

This process is also applicable to perfluoroketones free from ether groups, and in this case it yields perfluorinated hydrocarbons. Ther perfluoroderivatives prepared from the ketones I have in both cases a high resistance to chemicals, especially to bases.

Depending on the chosen reaction components II and III, inert liquids I which have a boiling point in the range of from about 100 to 500° C., may be prepared according to the invention. These liquids may be used as heat transferring agents if they have a low molecular weight and as lubricants, if they have a high molecular weight.

It is an advantage of the process of the invention that it enables a homogenous final product to be prepared from homogenous starting materials even of high molecular weight. In contrast, in the known polymerization of hexafluoropropene epoxide or tetrafluoroethylene epoxide, a number of products having a different degree of polymerization is always obtained. This uniformity is desirable in most cases.

This is the case, for example when using heat transferring agents for soldering processes. This process designated as "Condensation soldering" has been presented to the public in 1974 (R. C. Pfahl, J. C. Mollendorf, T. Y. Chu, NEPCON WEST, 1974). According to this process, a liquid having a high boiling point is heated to the boil. When an object is plunged into the saturated vapor, the latter condenses, whereby the object is rapidly heated to the boiling point of the liquid. The boiling point of the liquid is chosen so that the desired metal parts, for example the solder on printed circuit connections, melt. On the other hand, sensitive spots must not be damaged thermally. The liquid must be non-combustible, chemically and thermally inert, and non-toxic.

Fluorinated polyoxypropylene (molar weight 950, boiling point 224° C.), for example, has been proposed for junctions soldered with an alloy having a melting point of 183° C. (60% of tin, 40% of lead). As mentioned above, ketones of the formula I may also be used for this process. By varying the radicals $R_1'$ and $R_2$, the boiling point of the liquid may be adjusted to the melting point of the corresponding metal.

If salts and acid fluorides having about the same molecular weight are used as starting compounds, a ketone having about the double molar weight will be obtained. This is also the case when high-molecular weight starting compounds are used, for example a polymeric hexafluoropropene epoxide. These polymers still possess a terminal acid fluoride group, which may be converted in known manner into the salt of the corresponding carboxylic acid. The salt obtained of the formula II may subsequently be reacted with further portions of the originally used acid fluoride according to the process of the invention.

By reacting these high-molecular weight acid fluorides, which can be readily prepared from perfluorinated epoxide, with the analogous salts, perfluorinated ethers having a molecular weight of up to about 4500, may be prepared, ethers of a molecular weight of about 2000 being obtained in especially good yields.

Suitable feed products of defined molecular weight are in particular the following oligomeric acid fluorides of the formula III (or the salts III which may be prepared from these fluorides):

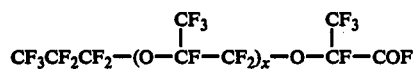

wherein x is an integer of from 1 to 6, preferably of from 2 to 4, as well as

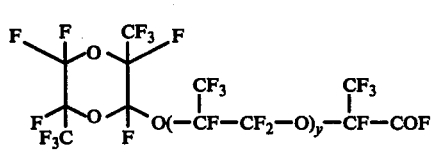

wherein y is an integer of from 0 to 5, preferably of from 1 to 3.

The latter derivatives of dioxane wherein y is 0 or 1 may be readily prepared from hexafluoropropene epoxide according to the process disclosed in German Offenlegungsschrift No. 2,461,445). By further adding epoxide in the presence of cesium fluoride in aprotic polar solvents, the homologous compounds wherein y is an integer of from 3 to 5, may be prepared from these acid fluorides (cf. German Offenlegungsschrift No. 2 517 357).

As has been mentioned above, the salts II may be prepared in situ by the action of certain basic compounds, for example alkali metal carbonates. The ketone synthesis thus modified is also carried out especially advantageously at a temperature of from 50 to 180° C., especially of from 70 to 180° C., preferably of from 100 to 150° C. Suitable carbonates are the corresponding compounds of lithium, sodium, potassium, rubidium and cesium. Mixtures of these carbonates may also be used.

The process according to the invention is generally performed in the following manner: About 1 equivalent of perfluorocarboxylic acid fluoride per equivalent of alkali metal salt is added to a suspension of the alkali metal salt of the mineral acid or of oxalic or formic acid, in an aprotic polar solvent, at a temperature of from 20 to 200° C., preferably of from 50 to 180° C.

When using carbonates, generally the double molar quantity of acid fluoride is added to a suspension of the alkali metal carbonate in an aprotic polar solvent at a temperature of from 20 to 200° C., in accordance with the reaction equation. The quantity of alkali metal salt is not critical and may be in the range of from 0.1 to 10 mols per mol of acid fluoride. An excess of alkali metal carbonate, for example of from 100 to 200 mol %, may be used.

When using less reactive acid fluorides, i.e. compounds containing 2 or more ether groups, for example those of the formula IIIa wherein x is > 1, the quantity of the alkali metal salt is not very critical. In this case, an excess of up to 100% of the theoretical quantity of the alkali metal salt may be used.

A particular variant of the process comprises the use of an excess of the acid fluoride. It has been ascertained that perfluorovinyl ethers may be obtained as by-products, when using polymers of hexafluoropropane epoxide, especially polymers of an oligomerization degree of more than 5. These perfluorovinyl ethers react in the presence of formed alkali metal fluoride with the acid fluoride used in excess thus yielding the desired ketones. This reaction may be accelerated by the addition of CsF.

When using reactive acid fluorides, i.e., compounds contain a small number of ether groups, for example perfluoroalkylpropionyl-fluorides and perfluoroalkoxypropionyl-fluorides (formula IIIa with x being 0), only the theoretically required quantity of alkali metal salt should be used, otherwise with an increasing amount of alkali metal salt, the quantity of formed perfluoroolefins would increase thus decreasing the amounof the desired perfluoroketone. The same applies for compounds of the formula IIIa with x being 1. Especially high yields are obtained, independent of the alkali metal salt used, if the process according to the invention is carried out under conditions which prevent the escaping of optionally formed small quantities of the perfluoro-vinyl compound from the reaction system. This may be achieved by operating in a closed vessel (autoclave) or by using a reflux condenser, or more simply by keeping the reaction temperature so low that the boiling temperature of the corresponding perfluorovinyl compounds is not attained.

In first approximation, the boiling point of the vinyl compound is by 5340:M (° C.) lower than the boiling point of the corresponding perfluorocarboxylic acid fluoride (having the molecular weight M).

In the process disclosed in U.S. Pat. No. 3,291,843 (Examples 13 to 17) only the perfluorovinyl ether, and not the perfluoroketone was obtained from alkali metal carbonate and perfluorocarboxylic acid fluoride. This different result is caused by the different feed quantity of alkali metal salt and by the different mode of operation (distilling off of the vinyl ether).

The end of the reaction may be readily seen by the fact that the acid fluoride band has either completely disappeared in the infra-red spectrum at 5.3μ or, when using an acid fluoride excess, is no longer diminished. When using a carbonate, formate or sulfite, the end of the reaction may be seen by the fact that gases are evolved no longer.

When working with an excess of acid fluoride in the range of from 5 to 30%, preferably of from 10 to 20%, acid fluoride which has not reacted may in most cases be distilled off from the ketone formed and be recovered owing to its lower boiling point.

The quantity of solvent is not critical even when applying alkali metal salts of a mineral acid or of formic or oxalic acid. The quantity of solvent is generally in the range of from 0.1 to 10, in particular of from 0.2 to 2 parts by volume per part of acid fluoride.

The process will be illustrated in the following examples:

EXAMPLE 1

Perfluoro-2,4-bis-(3',6'-dimethyl-1',4'-dioxan-2'-oxy)-pentanone-3

In a three-necked agitator flask provided with a reflux condenser, a stirrer and a thermometer, 165 g (0.32 mol) of K-perfluoro[α-3,6-dimethyl-1,4-dioxanyl-2-oxy-propionate], 60 ml of tetraglyme and 165 g of perfluoro[α-(3,6-dimethyl-1,4-dioxanyl-2-oxy)-propionic acid fluoride] (0.34 mol) are stirred for 8 hours at 130° C. The heavy phase of the reaction mixture is separated, washed with 100 ml of aceton and distilled. (Boiling point of from 219° to 221° C.).

There are obtained 234 g (81.8% of the theory, calculated on potassium salt used) of the compound of the formula

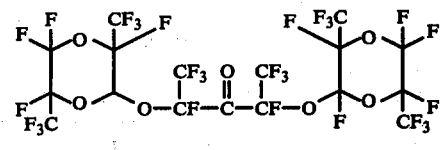

Kp.: 219° - 221° C the structure of which has been confirmed by analysis, and by infra-red, NMR and mass spectra.

EXAMPLE 2

Perfluoro-5,7-dimethyl-4,8-dioxa-undecanone-6

A mixture of 140 g (0.37 mol) of K-perfluoropropoxypropionate, 92 g (0.277 mol) of perfluoropropoxypropionic acid fluoride and 60 ml of tetraglyme is shaken for 24 hours at 130° C. in a 500 ml autoclave. After cooling the pressure in the autoclave is released, the heavier phase which has been separated, is washed with 100 ml of acetonitrile and distilled. There are obtained 98.5 g (corresponding to 59.5% of the theory, calculated on acid fluoride used) of the compound of the formula

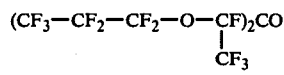

having a boiling point of from 140° to 148° C.

EXAMPLE 3

Perfluoro-5,8,11,16,19,22,25-octamethyl-4,7,10,13,17,20,23,26-octaoxa-nonacosanone-15

70 g (0.081 mol) of a salt of the formula

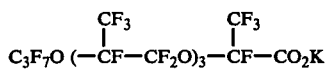

(which has been prepared from pentameric hexafluoropropeneepoxide by saponification and neutralization with potassium hydroxide), 30 ml of tetraglyme and 51 g of the acid fluoride of the same perfluorocarboxylic acid are stirred in a glass flask for 8 hours at 130° C. The product is shaken with 100 ml of acetonitrile and the lower phase is separated. The latter is diluted with 50 ml of trifluorotrichloroethane and the lighter phase which forms thereby is separated. From the lower phase there are obtained, after distillation of trifluorotrichloroethane, 87 g of the ketone of the formula

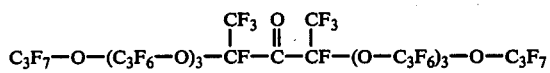

which is pure, according to IR-spectroscopy.

Further 7 g of the ketone precipitate from the separated tetraglyme phase, when the latter is diluted with 100 ml of water. The total yield of ketone is, consequently, 96.6% of the theory. The boiling point is in the range of from 175° to 180° C.

EXAMPLE 4

Perfluoro-[4-methyl-2-(3',6'-dimethyl-1',4'-dioxan-2'-yl-oxy)-nonanone-3]

82.8 g of perfluorooctanoic acid (0.197 mol) are neutralized with a 20% aqueous KOH-solution to a pH of 6 and the salt mixture formed by octanoate and KF is dried for 24 hours at 100° C./1 mbar. Thereafter 70 ml of tetraglyme are added. After addition of 100 g of perfluoro-(3,6-dimethyl-1,4-dioxanyl-2-oxy)-propionic acid fluoride, the mixture is stirred for 15 hours and the product mixture is treated as in Example 1. By distillation there are obtained 102 g (62.2% of the theory, calculated on used perfluorooctanoic acid) of the compound of the formula

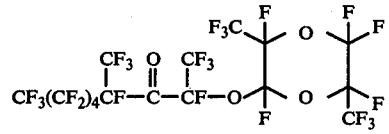

having a boiling point of from 210° to 222° C., the structure of which is confirmed by the analysis and by spectroscopic data.

EXAMPLE 5

To 116 g of a carboxylic acid fluoride of a boiling point of from 62° to 104° C. which has been prepared by polymerization of hexafluoropropene epoxide and of 96 g of the potassium salt prepared therefrom there are added 100 ml of tetraglyme and the mixture obtained is stirred at 130° C. After 15 hours there are obtained 81 g of a ketone mixture having a boiling range of from 80° to 140° C./0.2 mbar, by distillation of the separated fluoro-organic phase, besides acid fluoride which has not reacted. This mixture is free from acid fluoride and in the IR-spectrum is show an C=O-absorption of the carbonyl ether group at 5.62μ.

EXAMPLE 6

To 53.4 g of perfluoro-K-n-propoxy-propoxypropionate (0.10 mol) of the formula

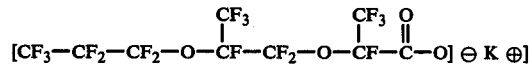

which are dissolved or suspended in 50 ml of tetraglyme there are added while stirring, at 50° C., 47.6 g of perfluoro-(3,6-dimethyl-1,4-dioxanyl-2-oxy-propionic acid fluoride). After 60 hours, about 80% of the acid fluoride have reacted according to the IR-spectrum. After 84 hours the acid fluoride band at 5.3μ has disappeared and the keto band at 5.6μ has appeared. The separated lower phase of the reaction mixture is washed with 50 ml of H$_2$O, is dried and distilled.

There are obtained 71 g (78.2% of the theory) of a perfluoro-[2-(3',6'-dimethyl-1',4'-dioxan-2'-yl-oxy)-4,7-dimethyl-5,8-dioxa-undecanone-3-] having a boiling point of from 210° to 217° C.

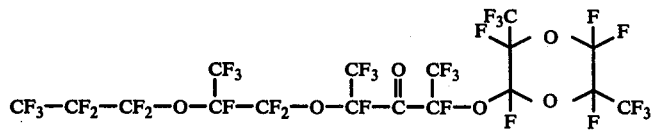

The structure is confirmed by the IR- and mass spectra and by the analysis.

EXAMPLE 7

Preparation of perfluoro-2,4-bis-(3',6'-dimethyl-1',4'-dioxa-2-oxy-)pentanone-3 with the use of the sodium salt The sodium salt prepared from 100 g (0.21 mol) of perfluoro-3,6-dimethyl-1,4-dioxanyl-2-oxy-propionic acid fluoride by saponification with H$_2$O and neutralization with aqueous NaOH is suspended in 60 ml of tetraglyme after drying at 100° C./1 mbar. At 100° C. there are added dropwise while stirring 160 g (0.36 mol) of the above acid fluoride. After stirring for 5 hours at 130°

C. there are added to the product mixture after cooling 500 ml of acetonitrile and the forming heavier phase is separated together with the NaF formed. NaF is suction-filtered and the fluoro-organic phase is distilled.

There are obtained 54 g of perfluoro-3,6-dimethyl-1,4-dioxanyl-2-oxy-propionic acid fluoride and 129 g of ketone (boiling point of from 215° to 221° C.), corresponding to a yield of 69.4% of the theory.

EXAMPLE 8

To 56 g of the anhydride of perfluoro-α-[2-n-propoxypropoxy]-propionic acid of the formula

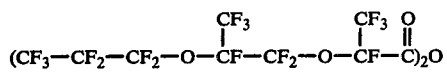

which have been prepared by dehydratation of the acid by means of $P_2O_5$, there are added 50 ml of tetraglyme and the mixture obtained is stirred for 7 hours at a temperature of 125° C. in the presence of 20 g of KF. The heavier phase which forms is separated and KF is filtered off. By distillation there are obtained 34 g of perfluoro-[bis-(5-methyl-3,6-dioxa-nonyl-2)-ketone] having a boiling range of from 216° to 220° C. (63.5% of the theory) and having the formula

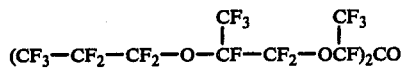

EXAMPLE 9

To 13 g of the silver salt of perfluorooctanoic acid (0.025 mol) and 10 ml of tetraethylene-glycol-dimethyl ether there are added 20 g of perfluoro-3,6-dimethyl-2,4-dioxanyl-2-oxy-propionic acid fluoride (0.042 mol) and the resulting mixture is stirred for 20 hours at 110° C.

By distillation there are obtained 3.5 g (17%) of perfluoro-[4-methyl-2-(3',6'-dimethyl-1',4'-dioxan-2'-yloxy)-nonanone-3].

EXAMPLE 10

Perfluoro-2,4-bis-(3',6'-dimethyl-1',4'-dioxanyl-2'-oxy)-pentanone-3

In an agitator vessel, provided with a dropping funnel, a thermometer and a condenser, 300 g (0.63 mol) of perfluoro-α-perfluoro-α-(3,6-dimethyl-1,4-dioxanyl-2-oxy)-propionic acid fluoride are added at a temperature of 100° C. to a suspension of 60 g of $K_2CO_3$ (0.435 mol) in 200 ml of tetraglyme and the resulting mixture is stirred for 5 hours at 130° C. Thereafter starting material is present no longer. After cooling, the formed heavier phase (230 g) is separated. To the upper solvent phase there are added 200 ml of $H_2O$. Thereby another 8 g of reaction product precipitate which are distilled with the main quantity of the reaction product.

There are obtained 226 g (81% of the theory) of the compound of the formula

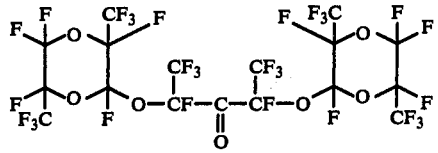

having a boiling point of from 216° to 221° C.

EXAMPLE 11

Perfluoro-di-(5-methyl-3,6-dioxa-nonyl-2)-ketone

As described in Example 10 50 g (0.10 mol) of perfluoro-α-(2-n-propoxy-propoxy)-propionic acid fluoride are added dropwise to 10 g of $K_2CO_3$ in 50 ml of tetraglyme at 130° C. This mixture is stirred for 5 hours. After cooling, the heavier phase is separated, the upper phase is diluted with water as indicated in Example 10 and the precipitating fluoro-organic phase is distilled together with the main qunatity (36.5 g).

There are obtained 31 g (66.7% of the theory of the compound

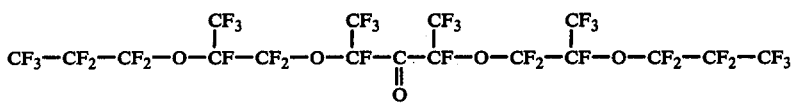

having a boiling range of from 60° to 61° C./0.3 mbar.

EXAMPLE 12

In analogous manner to Example 11, 10 g of $Na_2CO_3$ are suspended in 30 ml of tetraglyme. Perfluoro-α-(3,6-dimethyl-1,4-dioxanyl-2-oxy)-propionic acid fluoride (50 g) is added thereto at 100° C. and the resulting mixture is stirred at 130° C. for 16 hours.

After treating the reaction mixture there are obtained 39.5 g (84.8% of the theory) of the ketone of Example 10.

EXAMPLE 13

332 g of a hexafluoropropene-epoxide oligomer having a boiling range of from 220° to 260° C. and corresponding to the formula

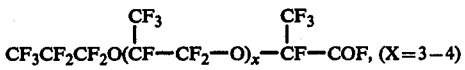

are slowly added dropwise to a suspension of 60 g of $K_2CO_3$ in 200 ml of tetraglyme at 130° C. and the resulting mixture is stirred for 2 hours at this temperature. To the product mixture there are added 200 ml of acetonitrile and the formed lower phase is removed. The potassium salt is filtered off, and the reaction product is distilled. There are obtained three fractions:

1st fraction having a boiling range of from 45° C./0.3 mbar to 80° C./0.4 mbar
2nd fraction having a boiling range of from 80° C./0.4 mbar to 140° C./0.4 mbar
3rd fraction having a boiling range of from 140° C./0.4 mbar to 165° C./0.4 mbar.

The fraction (1) consists of oligomers having a terminal vinyl ether group (3). Fraction (3) consists, as it has been confirmed by IR-spectroscopy, of the desired ketone. The fraction (2) consists of the compounds (1) and (3) in a ratio of 1:1.

EXAMPLE 14

To 10 g of $K_2CO_3$ (0.072 mol) and 3 g of CsF in 60 ml of tetraglyme placed in the same apparatus as in Example 10 there are added dropwise at 100° C. 150 g (0.167 mol) of a hexafluoropropene epoxide oligomer having an average molecular weight of about 900 (boiling point of from 170° to 300° C.). Stirring is continued at the same temperature for 2 hours.

After cooling to room temperature 20 ml of acetonitrile are added, the product mixture is shaken and the precipitating lower phase, which contains KF and tetraglyme, is distilled. After having distilled off 10 g of oligomer which has not reacted there are obtained 110 g of pure ketone having a boiling point of from 70° to 140° C./0.5 mbar, which corresponds to a yield of about 82%, calculated on reacted oligomer.

EXAMPLE 15

Example 11 is repeated but a reaction temperature of only 50° C. is chosen. After a reaction time of 20 hours, the absorption band of the acid fluoride at 5.3μ has completely disappeared in favor of the keto band at 5.6μ according to the IR-spectroscopy.

EXAMPLE 16

Perfluoro-6-methyl-tetradecanone-7

To a suspension of 50 ml of tetraglyme and 20 g of $K_2CO_2$ placed in the agitator vessel of Example 10 there are added first 0.2 g of CsF and thereafter dropwise 100 g of perfluoro-octanoic acid fluoride, at a temperature of from 100° to 110° C. The product mixture is stirred for 60 hours at a temperature of from 100° to 110° C. The product mixture obtained is distilled. Besides 20 g of acid fluoride which has not reacted there are obtained 32 g of perfluoro-6-methyl-tetradecanone-7 having a boiling range of from 210° to 212° C. The following structure is confirmed by the IR and mass spectra and by the elementary analysis:

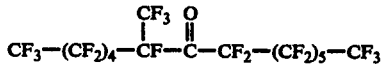

EXAMPLE 17

Perfluoro-2,4-bis-(3',6'-dimethyl-1,4-dioxan-2'-oxy)-pentanone-3 (ketone 1) from $Na_2B_4O_7$ and perfluoro-[α-(3,6-dimethyl-1,4-dioxanyl-2-oxy)-propionic acid fluoride] (DOPF)

50 g of DOPF (0.105 mol) are added to 20 g of anhydrous $Na_2B_4O_7$ (0.099 mol) which are placed in an apparatus provided with a stirrer, a thermometer, a condenser and a dropping funnel, at a temperature of 120° C. and the product mixture is stirred at the same temperature for 46 hours. $CO_2$ escapes in the course of the reaction. The product mixture is distilled and there are obtained 34.5 g of ketone 1 and 8.5 g of un-reacted acid fluoride. The yield, calculated on reacted acid fluoride, is 89.4%.

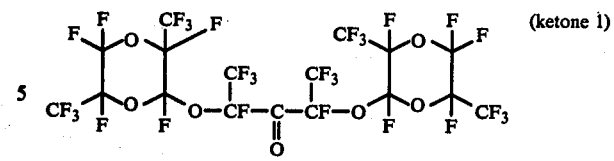

EXAMPLE 18

As in example 17, 47.6 g of DOPF (0.1 mol) are added dropwise to a mixture of 10 g of K-oxalate (0.06 mol) and 30 ml of tetraglyme at 100° C. and the product mixture is stirred for 4 hours at this temperature. By distilling the mixture, there are obtained 38 g of ketone 1, which corresponds to a yield of 86%.

EXAMPLE 19

To a suspension of 17 g of K-formiate (0.20 mol) in 60 ml of tetraglyme there are added 100 g of DOPF (0.21 mol) at 100° C. and the mixture is stirred for 10 hours at this temperature. By distillation of the product mixture 56 g of ketone 1 may be isolated (60.1%).

EXAMPLE 20

Perfluoro-bis-(5-methyl-3,6-dioxa-nonyl-2)-ketone (ketone 2) from Na-m-silicate $Na_2SiCO_3$ and perfluoro-α-(2-n-propoxy-propoxy-propionic acid fluoride To 20 g of $Na_2SiO_3$ (0.164 mol) and 30 ml of tetraglyme there are added 50 g of the above acid fluoride (0.1 mol) at a temperature of 110° C. and the mixture is stirred for 4 and a half hours at this temperature. By distilling the mixture there are obtained besides 7 g of un-reacted acid fluoride 26 g of ketone, which corresponds to a yield of 65.0%, calculated on reacted acid fluoride

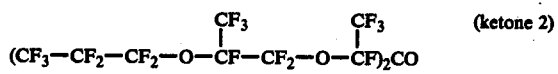

EXAMPLE 21

50 g of DOPF (0.105 mol) are added to 30 g of $Na_2PO_3$ (0.207 mol) and 50 ml of tetraglyme at a temperature of 110° C. and the mixture is stirred for 2 hours at this temperature. By distilling the mixture there are obtained 18 g (38.7%) of ketone 1.

EXAMPLE 22

Ketone 2 from perfluoro-α-(2-n-propoxy-propoxy)-propionic acid fluoride and $K_2SO_3$ 48 g of the above acid fluoride (0.096 mol) are added to a suspension of 20 g of $K_2SO_3$ (0.126 mol) and 50 ml of tetraglyme at a temperature of 120° C. and the mixture is stirred at 130° C. for 74 hours. By distillation there are obtained 14 g of ketone 2, which corresponds to a yield of 31.2%.

EXAMPLE 23

50 g of DOPF (0.105 mol) are added to 35 g of $NaIO_3$ (0.176 mol) and 30 ml of tetraglyme at a temperature of 110° C. and the mixture is stirred at the same temperature for 2 hours. Distillation of the product mixture yields 5.5 g of ketone 1.

EXAMPLE 24

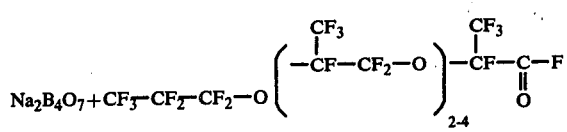

50 g of a mixture of equal parts by weight of (HFPO)$_4$ and (HFPO)$_5$ are added to 20 g of Na-tetraborate (0.099 mol) and 30 ml of tetraglyme and the mixture is stirred for 70 hours at 150° C. Distillation of the mixtures yields 40 g of a ketone mixture having a boiling point of from 75° to 110° C./1 mbar.

What is claimed is:

1. A process for the preparation of aliphatic perfluoroketones, which comprises reacting a perfluorocarboxylic acid salt of the formula $$R_1 - CO_2M \qquad \text{II}$$

wherein M is a metal selected from the group consisting of Li, Na, K, Rb, Cs, Ag and R$_1$ is a perfluoroalkyl radical having of from 2 to 50 carbon atoms, which radical may contain in addition one or more ether oxygen linkages, with a perfluorocarboxylic acid fluoride of the formula $$R_2 - COF \qquad \text{III}$$

wherein R$_2$ is a perfluoroalkyl radical having of from 1 to 50 carbon atoms, which radical may contain in addition one or more ether oxygen linkages, in an aprotic-polar solvent at a temperature of from 20° to 200° C. to form a ketone of the formula R$_2$COR$_3$ wherein R$_3$ is selected from R$_1$ and isomers of R$_1$.

2. Process as claimed in claim 1, which comprises preparing the salts of the formula II in an aprotic-polar solvent by the action of an acid fluoride of the formula R$_1$-COF on an alkali metal salt of formic acid or of oxalic acid or of a mineral oxygen acid, the central atom of which is an element of the groups IIIA to VIIA of the periodic table and which is weaker than trifluoroacetic acid at a temperature of from 20° to 200° C.

3. Process as claimed in claim 1, which comprises preparing the mixture of perfluorocarboxylic acid salt II and acid fluoride III by reacting a perfluorocarboxylic acid anhydride (R$_1$CO)$_2$O with an alkali metal fluoride in an aprotic polar solvent at a temperature of from 20° to 200° C.

4. Process as claimed in claim 2, which comprises using as salt of a mineral oxygen acid an alkali metal carbonate of the formula M$_2$CO$_3$.

* * * * *